United States Patent
Morita et al.

(10) Patent No.: US 6,174,523 B1
(45) Date of Patent: Jan. 16, 2001

(54) HAIR CUTICLE CARING METHOD

(75) Inventors: Kouzi Morita; Yoshimasa Okamoto; Hiroto Tanamachi; Shunsuke Watabe; Yoshihisa Kitano; Yuji Ishino; Naoki Satoh; Takeshi Iizaki, all of Tokyo (JP)

(73) Assignee: Kao Corporation, Tokyo (JP)

( * ) Notice: Under 35 U.S.C. 154(b), the term of this patent shall be extended for 0 days.

(21) Appl. No.: 09/206,293

(22) Filed: Dec. 7, 1998

(30) Foreign Application Priority Data

Dec. 8, 1997 (JP) .................................................. 9-337053
Jul. 22, 1998 (JP) ................................................ 10-206047
Jul. 22, 1998 (JP) ................................................ 10-206048

(51) Int. Cl.$^7$ ................................ A61K 7/06; A61K 7/08
(52) U.S. Cl. .................. 424/70.28; 424/70.1; 424/70.27
(58) Field of Search ........................................... 424/70.28

(56) References Cited

U.S. PATENT DOCUMENTS

| | | | |
|---|---|---|---|
| 4,294,728 | * 10/1981 | Vanlerberghe et al. | 252/542 |
| 4,436,722 | * 3/1984 | Matsunaga et al. | 424/70 |
| 5,009,880 | * 4/1991 | Grollier et al. | 424/47 |
| 5,403,517 | * 4/1995 | Horinishi et al. | 252/551 |
| 5,635,469 | * 6/1997 | Fowler et al. | 510/406 |

* cited by examiner

Primary Examiner—Thurman K. Page
Assistant Examiner—P. E. McQueeney
(74) Attorney, Agent, or Firm—Oblon, Spivak, McClelland, Maier & Neustadt, P.C.

(57) ABSTRACT

The present invention relates to a hair cuticle caring method or volume enhancing method, which comprises treating hair with a composition containing (A) a cationic surfactant and (B) an organic acid or salt thereof in a combination to give, when an aqueous solution containing 1 mM of each of the components is formed, 40 mN/m or less as the surface tension of the aqueous solution at 27±0.5° C. By the application of the above-described composition, the lift-up of the hair cuticle can be suppressed, the volume can be enhanced softly, moisturized but stickiness-free feeling is imparted and styling ease is improved.

13 Claims, No Drawings

HAIR CUTICLE CARING METHOD

TECHNICAL FIELD

The present invention relates to a hair cuticle caring method which suppresses peeling of hair cuticles.

BACKGROUND ART

A cationic surfactant is a component indispensable for improving touch feeling of hair, but it sometimes causes a peeling phenomenon (which will hereinafter be called "lift-up") of hair cuticles, thereby damaging the surface of the hair and decreasing a gloss thereon.

An object of the present invention is to provide a hair cuticle caring method for suppressing the lift-up of hair cuticles.

DISCLOSURE OF THE INVENTION

In the present invention, there is thus provided a hair cuticle caring method comprising treating hair with a composition which contains (A) a cationic surfactant and (B) an organic acid or salt thereof in combination to give, when an aqueous solution containing 1 mM of each of said components is formed, 40 mN/m or less as the surface tension of said aqueous solution at 27±0.5° C.

According to the process of the present invention, the lift-up of hair cuticles can be suppressed and moreover, the volume of hair can be enhanced softly without hardening the hair. The present invention therefore provides a method for enhancing the volume of hair, which comprises treating the hair with the above-described composition. In addition, the process of the present invention makes hair free from oiliness and provides the hair with moisturized but stickiness-free feeling and styling ease.

BEST MODES FOR CARRYING OUT THE INVENTION

Examples of the cationic surfactant to be used as the component (A) in the present invention includes quaternary ammonium salts each represented by the following formula (1):

$$\left[ R^1 - \underset{\underset{R^3}{|}}{\overset{\overset{R^2}{|}}{N}} - R^4 \right]^+ Z^-  \quad (1)$$

wherein at least one of $R^1$, $R^2$, $R^3$ and $R^4$ represents an alkyl or alkenyl group which may be substituted by an alkoxy, alkenyloxy, alkanoylamino or alkenoylamino group having 8 to 35 carbon atoms in total or an aliphatic acyloxy (polyethoxy)ethyl group; the other one(s) each represents a benzyl group, a $C_{1-5}$ alkyl or hydroxyalkyl group or a polyoxyethylene group in which the number of moles added is not greater than 10 in total; and $Z^-$ represents a halogen ion or organic anion.

Among the above-described cationic surfactants, preferred examples include distearyldimethylammonium chloride, stearyltrimethylammonium chloride, capryltrimethylammonium chloride, myristyltrimethylammonium chloride, cetyltrimethylammonium chloride, behenyltrimethylammonium chloride, lauryltrimethylammonium chloride, N-stearyl-N,N,N-tri(polyoxyethylene)ammonium chloride (addition of 3 moles in total), cetylbenzyldimethylammonium chloride, cetyltriethylammonium bromide and distearyldimethylammonium chloride and in addition, branched quaternary ammonium salts represented by the below-described formula (2) and (3), respectively and quaternary ammonium salts represented by the below-described formula (4).

(2)

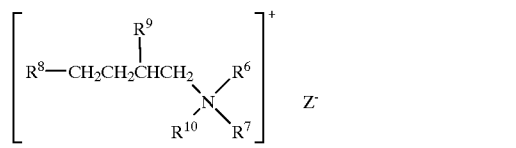

(3)

[wherein $R^5$ represents a mixture of (A) a branched alkyl group represented by formula:

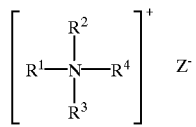

in which $R^{11}$ represents a methyl or ethyl group, c stands for an integer to give the number of carbon atoms 8 to 16 in total) and (B) a linear alkyl group represented by the formula: $CH_3-(CH_2)_d-$ (in which d stands for an integer of 7 to 15), the branching ratio of (A)/(A)+(B) being 10 to 100 mole %; $R^6$ and $R^7$ each represents a benzyl group, a $C_{1-3}$ alkyl group or a hydroxyalkyl group; $R^8$ and $R^9$ each represents a $C_{2-12}$ alkyl group, $R^{10}$ represents a group

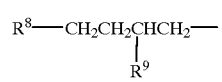

or a $C_{1-3}$ alkyl group, and $Z^-$ represents a halogen ion or an organic anion.

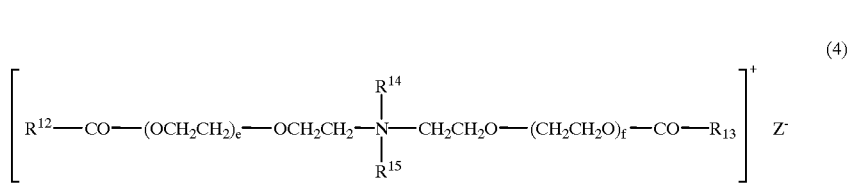

(4)

wherein $R^{12}$ and $R^{13}$ each represents a $C_{8-22}$ alkyl or alkenyl group which may be substituted by a hydroxyl group, $R^{14}$ and $R^{15}$ each represents a $C_{1-3}$ alkyl group or a group —(CH$_2$CH$_2$O)$_g$H (in which g stands for 1 to 6), e and f each stands for 0 to 5 and Z$^-$ represents a halogen ion or an organic anion.

Incidentally, specific examples of Z$^-$ which is a counter ion of these quaternary ammonium salts include halogen ions such as chlorine, iodine and bromine; and organic anions such as methosulfate, ethosulfate, methophosphate and ethophosphate. Anions of the organic acid as the component (B) may also be employed.

Among them, the branched quaternary ammonium salt represented by the formula (2) is ordinarily synthesized, for example, with a C$_{8-16}$ oxoalcohol as a raw material. Examples include dialkyldimethylammonium salts, dialkylmethylhydroxyethylammonium salts and dialkylmethylbenzylammonium salts containing an alkyl group introduced from an oxoalcohol.

In the present invention, the branching ratio of R$^5$ in the formula (2) is ordinarily 10 to 100 mole %, with 10 to 50 mole % being particularly preferred. The number of the carbon atoms of R$^5$ in total is 8 to 16. R$^5$ is preferred to have a predetermined distribution of carbon atoms and that having the following distribution is particularly preferred:

C$_8$ to C$_{11}$: 5 mole % or less
C$_{12}$: 10 to 35 mole %
C$_{13}$: 15 to 40 mole %
C$_{14}$: 20 to 45 mole %
C$_{15}$: 5 to 30 mole %
C$_{16}$: 5 mole % or less Specific examples of such a branched quaternary ammonium salt include dialkyldimethylammonium chloride which contains a C$_{8-16}$ alkyl group having a branching ratio of 10 to 50 mole %.

The branched quaternary ammonium salt represented by the formula (3) is obtained by the synthesis using as a raw material a C$_{8-28}$ Guerbet alcohol represented by the formula:

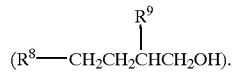

(R$^8$—CH$_2$CH$_2$CHCH$_2$OH).

Preferred examples of the branched quaternary ammonium salt include alkyl trimethylammonium salt, alkyl dimethylbenzylammonium salt, dialkyl dimethylammonium salt, dialkyl methylhydroxyethylammonium salt and dialkyl methylbenzylammonium salt, each having an alkyl group introduced from a Guerbet alcohol. Among them, particularly preferred are 2-dodecyltetradecyl trimethylammonium chloride, 2-dodecylhexadecyl trimethylammonium chloride, di-2-hexyldecyl dimethylammonium chloride and di-2-octyldodecyldimethylammonium chloride.

Examples of the quaternary ammonium salt represented by the formula (4) include those as described in WO93/10748, WO92/06899 and WO94/16677. Particularly, those of the formula (4) wherein R$^{12}$ and R$^{13}$ each represents an oleyl group or a C$_{12-18}$ alkyl group, R$^{14}$ represents a methyl group, R$^{15}$ represents a —CH$_2$CH$_2$OH group and e and f each stands for 0 are preferred.

As the component (A), at least one cationic surfactant can be used. It is preferably added in an amount of 0.01 to 20 wt. % based on the total composition. An amount of 0.1 to 10 wt. %, particularly 0.5 to 5 wt. % is preferred, because sufficient hair cuticle caring effects can be brought about and in addition, good feeling upon use and volume enhancing effects can be attained at such an amount.

Examples of the organic acid to be used as the component (B) in the present invention include carboxylic acids, sulfonic acids and phosphoric acid, more specifically, aromatic carboxylic acids such as salicylic acid and aromatic sulfonic acids such as 1-naphthalenesulfonic acid, 2-naphthalensulfonic acid, oxybenzonesulfonic acid and guaiazulenesulfonic acid.

Examples of the salt of an organic acid include alkali metal salts such as sodium and potassium and alkaline earth metal salts of calcium and magnesium.

As the component (B), sodium 1-naphthalenesulfonate, sodium 2-naphthalenesulfonate, sodium guaiazulenesulfonate, oxybenzonesulfonic acid and salicylic acid are preferred, with sodium 2-naphthalenesulfonate being particularly preferred.

Accordingly, the present invention further provides a hair cosmetic composition which comprises (A) a cationic surfactant and (B) at least one substance selected from the group consisting of 1-naphthalenesulfonic acid, 2-naphthalenesulfonic acid, guaiazulenesulfonic acid, oxybenzonesulfonic acid and salicylic acid and salts thereof. As the component (B), at least one organic acid or salt thereof can be used. Addition of it in an amount of 0.01 to 10 wt. %, particularly 0.05 to 5 wt. %, more particularly 0.1 to 3 wt. % based on the total composition is preferred because sufficient hair cuticle caring effects are brought about.

The component (B) may be added to the composition as an acid or salt or have been incorporated in the composition as a counter ion of the cationic surfactant.

In the present invention, the components (A) and (B) are used in combination to give, when an aqueous solution containing 1 mM of each of the components (A) and (B) is formed, not greater than 40 mN/m, preferably 39 to 20 mN/m, particularly preferably 38 to 25 mN/m as the surface tension of the aqueous solution at 27±0.5° C. The combination to give the surface tension exceeding 40 mN/m can suppress the lift-up of the hair cuticle. As the component (A) or the component (B), at least two substances may be used in combination. Upon combined use, an aqueous solution for the measurement of surface tension is prepared so that the total of at least two components (A) will be 1 mM and the total of at least two components (B) will be 1 mM.

In the present invention, the surface tension is measured by a surface tensiometer which adopts the ring method (the method as described in Kagaku Binran (Revised Fourth Edition) Basic part II-73). The term hair "cuticle caring" as used herein means suppression of the lift-up ratio of hair cuticles as judged by the below-described evaluation method (1) to less than 5% or less.

To the composition in the present invention, an oil component can be added further as a component (C). It is preferred because it can impart hair with good touch feeling such as moisturized feeling. Examples of such an oil component include saturated or unsaturated C$_{12-30}$ alcohols, ethers of such an alcohol and a polyhydric alcohol, esters of such an alcohol and a C$_{1-11}$ fatty acid, saturated or unsaturated C$_{12-30}$ fatty acids, esters of such a fatty acid and a monohydric or polyhydric alcohol, amides of such a fatty acid and an amine, sterols, squalane, phospholipid, glycolipid, animal or vegetable oils, hydrocarbons and mono-, di- or triglycerides composed of a saturated or unsaturated C$_{12-30}$ fatty acid.

Examples of the saturated or unsaturated C$_{12-30}$ alcohol include n-dodecanol, myristyl alcohol, cetyl alcohol, stearyl alcohol, oleyl alcohol, behenyl alcohol, ceryl alcohol, myricyl alcohol, caranabil alcohol, arachidic alcohol and octyl dodecanol. Examples of the polyhydric alcohol which can form an ether with one of the above-described alcohols include glycerin and polyalkylene glycol. Examples of the ether include α-monoisostearylglyceryl ether, polyoxyethylene polyoxypropylene stearyl ether, polyoxyethylene cetyl ether and polyoxyethylene octyldodecyl ether. Examples of the ester of such an alcohol and a $C_{1-11}$ fatty acid include cetyl 2-ethylhexanoate and diisostearyl malate.

Examples of the saturated or unsaturated $C_{12-30}$ fatty acid include lauric acid, myristic acid, palmitic acid, stearic acid, isostearic acid, behenic acid, cerotic acid, coconut oil fatty acid, oleic acid and 18-methyleicosanoic acid. Examples of the monohydric or polyhydric alcohol which can form an ester with such a fatty acid include the above-described saturated and unsaturated $C_{12-30}$ alcohols, glycerin, sterol and fat soluble vitamins. Examples of the ester include oleic monoglyceride, palmitic monoglyceride, behenic monoglyceride, myristic monoglyceride, isostearic monoglyceride, diglyceryl isostearate, polyoxyethylene glyceryl monoisostearate, isopropyl myristate, cholesteryl isostearate and dipentaerythrite fatty acid ester. Examples of the amide of the above-described fatty acid and an amine include fatty acid dialkylaminoalkylamide (long-chain amidoamine), more specifically, stearic acid diethylaminoethylamide ("Amidoamine S"/Kao Corporation).

Examples of the phospholipid include soybean phospholipid, while that of the glycolipid include sohorose lipid ("Glycolipid PSL"/Kao Corp.). Examples of the hydrocarbon include vaseline, liquid paraffin and solid paraffin. Examples of the animal or vegetable oil and fat include mink oil, meadow-foam oil, olive oil (composed mainly of glycerin oleate), beeswax (composed mainly of an ester of myricyl alcohol and palmitic acid), palm oil (composed mainly of glycerin myristate), spermaceti (composed mainly of an ester of ceryl alcohol and palmitic acid) and wool grease (lanolin).

Examples of the mono-, di- or triglyceride of a saturated or unsaturated $C_{12-30}$ fatty acid include monolauric glyceride, monostearic glyceride, monooleic glyceride, dimyristic glyceride, 1-palmitoyl-oleic glyceride and tristearic acid glyceride.

Among them, aliphatic alcohols represented by the below-described formula (5), fatty acids represented by the below-described formula (6) and glycerides represented by the below-described formula (7) are preferred.

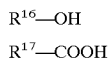  (5)

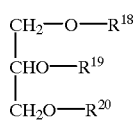  (6)

(7)

$$\begin{array}{l} CH_2-O-R^{18} \\ CHO-R^{19} \\ CH_2O-R^{20} \end{array}$$

wherein $R^{16}$ represents a $C_{12-22}$ alkyl or alkenyl group, $R^{17}$ represents a $C_{11-21}$ alkyl or alkenyl group and, in the formula (7), at least one of $R^{18}$, $R^{19}$ and $R^{20}$ represents a carbonyl group having a $C_{11-21}$ alkyl or alkenyl group and the other one(s) each represents a hydrogen atom.

As the component (C), at least one oil component can be used. It is preferred to add it in an amount of 0.01 to 30 wt. %, particularly 0.05 to 20 wt. %, more preferably 0.1 to 10 wt. % based on the total composition, because such an amount brings about sufficient hair cuticle caring effects and at the same time, good feeling upon use.

To the composition of the present invention, it is possible to add, for example, a surfactant other than the above-described one such as anionic surfactant, amphoteric surfactant and nonionic surfactant, anionic polymer, nonionic polymer, cationic polymer, alcohol, powders, functional beads capsules, metal chelating agent, antioxidant, viscosity modifier, antiseptic, animal or vegetable extract, anti-inflammatory, bactericide, anti-dandruff, oxidation inhibitor, pearling agent, ultraviolet absorber, pH adjuster, pigment and perfume within an extent not damaging the advantages of the present invention.

The composition used in the present invention can be prepared by mixing the components. There is no particular limitation imposed on its form and it can be obtained, for example, in the liquid, gel, cream or aerosol form.

The composition used in the present invention is preferred to have pH of 2 to 10, particularly pH 3 to 8. The composition is able to have a preferred pH only by controlling the amount of an acid or alkali to be incorporated therein.

In the process of the present invention, the composition comprising the above-described components (A) and (B) is applied directly to the hair and then spread over the hair, followed by the treatment ordinarily employed after rinsing or conditioning such as washing with water.

EXAMPLES

Example 1

An aqueous solution containing the cationic surfactant and organic acid or salt thereof as shown in Table 1 or 2, each 1 mM, was prepared and the surface tension was measured at 27±0.5° C. by using a surface tensiometer ("MODEL: K-14", product of KRUSS GmbH) which adopts the ring method. The results are shown in Tables 1 and 2.

TABLE 1

| Component (wt. %) | Invention product | | | | Comparative product |
|---|---|---|---|---|---|
| | 1 | 2 | 3 | 4 | 1 |
| Cetyl trimethylammonium chloride | 1 mM | 1 mM | 1 mM | 1 mM | 1 mM |
| Sodium 1-naphthalenesulfonate | 1 mM | — | — | — | — |
| Sodium 2-naphthalenesulfonate | — | 1 mM | — | — | — |
| Salicylic acid | — | — | 1 mM | — | — |
| Oxybenzonesulfonic acid | — | — | — | 1 mM | — |
| Deionized water | Balance | Balance | Balance | Balance | Balance |
| Total | 100 | 100 | 100 | 100 | 100 |
| Surface tension (mN/m) | 31.87 | 30.56 | 32.35 | 34.63 | 44.09 |

TABLE 2

| Component (wt. %) | Invention product | | | | | | | | Comparative product | |
|---|---|---|---|---|---|---|---|---|---|---|
| | 5 | 6 | 7 | 8 | 9 | 10 | 11 | 12 | 2 | 3 |
| Stearyltrimethylamoium chloride | 1 mM | 1 mM | 1 mM | 1 mM | — | — | 0.5 mM | — | 1 mM | 1 mM |
| Beheny trimethylammonium chloride | — | — | — | — | 1 mM | 1 mM | — | — | — | — |
| Cetyltrimethylammonium chloride | — | — | — | — | — | — | 0.5 mM | 1 mM | — | — |
| Sodium 1-naphthalenesulfonate | 1 mM | — | — | — | — | — | — | — | — | — |
| Sodium 2-naphthalenesulfonate | — | 1 mM | — | — | 1 mM | — | 1 mM | 0.5 mM | — | — |
| Oxybenzonesulfonic acid | — | — | 1 mM | — | — | — | — | — | — | — |
| Salicylic acid | — | — | — | 1 mM | — | 1 mM | — | 0.5 mM | — | — |
| Sodium isethionate | — | — | — | — | — | — | — | — | — | 1 mM |
| Deionized water | Balance | Balance | Balance | Balance | Balance | Balance | Balance | Balance | Balance | Balance |
| Total | 100 | 100 | 100 | 100 | 100 | 100 | 100 | 100 | 100 | 100 |
| Surface tension (mN/m) | 31.95 | 30.27 | 33.6 | 33.3 | 33.16 | 35.79 | 30.77 | 31.39 | 41.35 | 40.56 |

Example 2

A hair cosmetic composition was prepared mixing the components as shown in Table 3 and lift-up controlling effects and volume enhancing effects were evaluated. The results are shown in Table 3.
(Evaluation method)
(1) Lift-up controlling effects The hair cuticle care agent (1 g) was applied to 10 g of untreated hair of a Japanese female, followed by washing with water and drying. The hair was then observed at 20° C. and 65% RH by using a laser microscope VF-7510 (KEYENCE CORPORATION). The surface shape and roughness of the hair were measured. Among 100 uneven points sampled at random (an uneven point means a step difference of one hair cuticle), those having at least 0.7 $\mu$m as a step difference were counted. In accordance with the following equation, a lift-up ratio was calculated and indicated by the below-described standards.

$$\text{Lift-up ratio (\%)} = \frac{\text{The number of uneven points having a step difference of 0.7 } \mu\text{m or greater}}{\text{Uneven points in total (100)}} \times 100$$

A: A lift-up ratio 0 to 1%
B: A lift-up ratio 2 to 5%
C: A lift-up ratio 6 to 10%
D: A lift-up ratio 11% or greater
(2) Volume enhancing effects A tress of hair (with only hair root fixed) having a weight of 2.5 g, width of 2 cm and length of 10 cm was formed using the hair (untreated hair of a Japanese woman having an average cross-sectional area as narrow as $44 \times 10^{-10}$ m$^2$) sampled at random from women in their twenties to thirties. To the tress, 0.25 g of each composition was applied by hands, followed by rinsing for 15 seconds with warm water of 40° C. running at a flow rate of 1 liter/min. After natural drying (being allowed to stand) at 20° C. and 65% RH for 24 hours, the tress of the hair was fixed with the end portion, which was opposite to the hair root, being turned upward and the spreading width of the end portion of the tress was measured. Regarding the spreading width of the point portion of the hair as the enhanced volume, the volume enhancing effects were ranked by the following standards.

Volume enhancing effects (the width of the tress at the point portion after treatment)
A: Not less than 3.5 cm.
B: Not less than 3.3 cm but less than 3.5 cm.
C: Not less than 3.1 cm but less than 3.3 cm.
D: Less than 3.1 cm.

TABLE 3

| Component (wt. %) | Invention product | | | | | | | Comparative product | |
|---|---|---|---|---|---|---|---|---|---|
| | 13 | 14 | 15 | 16 | 17 | 18 | 19 | 4 | 5 |
| Stearyltrimethylammoium chloride | 2 | 3 | 5 | 3 | 5 | 1 | — | 2 | 2 |
| Cetyltrimethylammonium chloride | — | — | — | — | — | 2 | 3 | — | — |
| Sodium 2-naphthalenesulfonate | 1 | 1 | 1 | — | — | 1 | 0.5 | — | — |
| Oxybenzonesulfonic acid | — | — | — | 1 | — | — | — | — | — |
| Salicylic acid | — | — | — | — | 1 | — | 0.5 | — | — |
| Sodium glycolate | — | — | — | — | — | — | — | — | 1 |
| Cetyl alcohol | 3 | — | — | 3 | 3 | 3 | 3 | 4 | 3 |
| Palmitic monoglyceride | — | 3 | — | — | — | — | — | — | — |
| Myristic acid | — | — | 5 | — | — | — | — | — | — |
| Deionized water | Balance | Balance | Balance | Balance | Balance | Balance | Balance | Balance | Balance |
| Total | 100 | 100 | 100 | 100 | 100 | 100 | 100 | 100 | 100 |

TABLE 3-continued

|  | Invention product | | | | | | | Comparative product | |
|---|---|---|---|---|---|---|---|---|---|
| Component (wt. %) | 13 | 14 | 15 | 16 | 17 | 18 | 19 | 4 | 5 |
| Lift-up controlling effects | A | A | A | B | B | A | A | C | C |
| Volume enhancing effects | A | A | A | B | B | A | A | C | C |

Example 3

The compositions as shown in Tables 4 and 5 were prepared in a conventional manner. A tress (2.0 g) of hair (untreated hair of a Japanese woman having an average cross-sectional area as narrow as $44 \times 10^{-10}$ $m^2$) sampled at random from women in their twenties to thirties was formed. To the tress, 2 g of each composition was applied by hands. The tress was then rinsed for 15 seconds with warm water of 40° C. running at a flow rate of 1 liter/min, followed by drying naturally at 20° C. and 65% RH for 24 hours. The oiliness, moisturized feeling, stickiness-free feeling and styling ease were subjected to an organoleptic evaluation by a panel of 10 experts in accordance with the following standards. In accordance with the average points of 4.5 or greater, not less than 4 but less than 4.5, not less than 2.5 but less than 4 and less than 2.5, each of the compositions was ranked as A, B, C and D, respectively. The results are shown in Tables 4 and 5.

(Evaluation standards)
(1) Oiliness
   A: Absolutely free from oiliness
   B: Free from oiliness
   C: Average
   D: A little oily
   E: Oily
(2) Moisturized feeling
   A: Imparted with moisturized feeling very much
   B: imparted with moisturized feeling
   C: Average
   D: Not so imparted with moisturized feeling
   E: Not imparted with moisturized feeling
(3) Stickiness-free feeling
   A: Imparted with stickiness-free feeling very much
   B: Imparted with stickiness-free feeling
   C: Average
   D: Not so imparted with stickiness-free feeling
   E: Not imparted with stickiness-free feeling
(4) Styling ease
   A: Very easy styling
   B: Easy styling
   C: Average
   D: Not so easy styling
   E: Not easy styling

TABLE 4

|  | Invention product | | | | | | | | |
|---|---|---|---|---|---|---|---|---|---|
| Component (wt. %) | 22 | 23 | 24 | 25 | 26 | 27 | 28 | 29 | 30 |
| Stearyltrimethylammonium chloride | 2 | 2 | 3 | 5 | 1 | 2 | 2 | 2 | 2 |
| Dicetyldimethylammonium chloride | — | — | — | — | 2 | 1 | — | — | — |
| Sodium 2-naphthalenesulfonate | 1 | 1 | 1 | 1 | 2 | 0.5 | — | — | — |
| Oxybenzonesulfonic acid | — | — | — | — | — | — | 1 | — | — |
| Sodium guaiiazulenesulfonate | — | — | — | — | — | — | — | 1 | — |
| Salicylic acid | — | — | — | — | — | — | — | — | 1 |
| Cetyl alcohol | — | 3 | — | — | 3 | 3 | 3 | 3 | 3 |
| Palmitic monoglyceride | — | — | 3 | — | — | — | — | — | — |
| Myristic acid | — | — | — | 5 | — | — | — | — | — |
| Deionized water | Balance | Balance | Balance | Balance | Balance | Balance | Balance | Balance | Balance |
| Total | 100 | 100 | 100 | 100 | 100 | 100 | 100 | 100 | 100 |
| Oiliness | A | A | A | A | A | A | A | A | A |
| Moisturized feeling | B | A | A | A | A | A | A | A | A |
| Stickiness-free feeling | A | A | A | A | A | A | A | A | A |
| Styling ease | A | A | A | A | A | A | A | A | A |

TABLE 5

|  | Comparative Product | |
|---|---|---|
| Component (wt. %) | 6 | 7 |
| Stearyltrimethylammonium chloride | 2 | — |
| Dicetyldimethylammonium chloride | — | — |
| Sodium 2-naphthalenesulfonate | — | 2 |
| Oxybenzonesulfonic acid | — | — |
| Sodium guaiazulenesulfonate | — | — |
| Salicylic acid | — | — |
| Cetyl alcohol | 3 | — |
| Palmitic monoglyceride | — | — |
| Myristic acid | — | 5 |
| Deionized water | Balance | Balance |
| Total | 100 | 100 |
| Oiliness | C | D |
| Moisturized feeling | B | D |

TABLE 5-continued

| | Comparative Product | |
|---|---|---|
| Component (wt. %) | 6 | 7 |
| Stickiness-free feeling | B | D |
| Styling ease | C | D |

As is apparent from Tables 1 to 5, when the process of the present invention is applied, the lift-up of hair cuticles can be suppressed markedly and the volume of hair is enhanced softly without hardening of the hair. In addition, the hair becomes free from oiliness and is imparted with moisturized but stickiness-free feeling. This process also brings about excellent styling ease.

Japanese Patent Application Nos. 9-337053 filed on Dec. 8, 1997, 10-206047 and 10-206048 filed on Jul. 22, 1998, are incorporated herein by reference in its entirety.

What is claimed is:

1. A hair cosmetic composition, comprising:

a cationic surfactant (A) and at least one substance (B') selected from the group consisting of 1-naphthalenesulfonic acid, 2-naphthalenesulfonic acid, oxybenzonesulfonic acid, salicylic acid, guaiazulenesulfonic acid, a salt of 1-naphthalenesulfonic acid, a salt of 2-naphthalenesulfonic acid, a salt of oxybenzonesulfonic acid, a salt of salicylic acid, a salt of guaiazulenesulfonic acid, and mixtures thereof;

wherein the cationic surfactant (A) is a quaternary ammonium salt represented by formula (1):

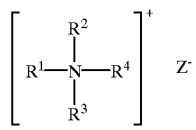

(1)

wherein at least one of $R^1$, $R^2$, $R^3$ and $R^4$ represents an alkyl or alkenyl group which may be substituted by an alkoxy, alkenyloxy, alkanoylamino or alkenoylamino group having 8 to 35 carbon atoms in total or an aliphatic acyloxy(polyethoxy)ethyl group, the other one(s) each represent a benzyl group, a $C_{1-5}$ alkyl or hydroxyalkyl group or a polyoxyethylene group;

wherein the number of repeat units of oxyethylene is not greater than 10 in total; and $Z^-$ is a halogen ion or organic anion.

2. A hair cosmetic composition according to claim 1, further comprising (C) an oil.

3. A hair cosmetic composition according to claim 2, wherein the oil (C) is selected from the group consisting of an aliphatic alcohol represented by formula (5), a fatty acid represented by formula (6) and a glyceride represented by formula (7):

$R^{16}$—OH  (5)

$R^{17}$—COOH (6)

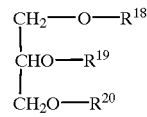

(7)

wherein $R^{16}$ is a $C_{12-22}$ alkyl or alkenyl group, $R^{17}$ is a $C_{11-21}$ alkyl or alkenyl group and, in formula (7), at least one of $R^{18}$, $R^{19}$ and $R^{20}$ is a carbonyl group having a $C_{11-21}$ alkyl or alkenyl group and the other one(s) each represents a hydrogen atom.

4. A method of treating hair, comprising:

applying a composition comprising (A) a cationic surfactant and (B) an organic acid or salt thereof to hair, wherein the organic acid or salt thereof is selected from the group consisting of 1-naphthalenesulfonic acid, 2-naphthalenesulfonic acid, oxybenzonesulfonic acid, salicylic acid, guaiazulenesulfonic acid, a salt of 1-naphthalenesulfonic acid, a salt of 2-naphthalenesulfonic acid, a salt of oxybenzonesulfonic acid, a salt of salicylic acid, a salt of guaiazulenesulfonic acid and mixtures thereof; and wherein an aqueous solution of 1 mM of (A) and 1 mM of (B) exhibits a surface tension of 40 mN/m or less at a temperature of 27±0.5° C.

5. The method of treating hair according to claim 4, wherein the cationic surfactant (A) is a quaternary ammonium salt represented by formula (1):

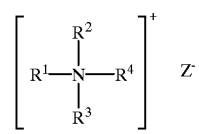

(1)

wherein at least one of $R^1$, $R^2$, $R^3$ and $R^4$ is an alkyl or alkenyl group which may be substituted by an alkoxy, alkenyloxy, alkanoylamino or alkenoylamino group having 8 to 35 carbon atoms in total or an aliphatic acyloxy (polyethoxy)ethyl group, the other one(s) each represent a benzyl group, a $C_{1-5}$ alkyl or hydroxyalkyl group or a polyoxyethylene group;

wherein the number of repeat units of oxyethylene is not greater than 10 in total; and $Z^-$ is a halogen ion or organic anion.

6. The method of treating hair according to claim 4, wherein the organic acid or salt thereof is selected from the group consisting of a carboxylic acid, a sulfonic acid, a salt of a carboxylic acid, a salt of a sulfonic acid, and mixtures thereof.

7. The method of treating hair according claims 4, further comprising (C) an oil.

8. The method of treating hair according to claim 7, wherein the oil (C) is selected from the group consisting of an aliphatic alcohol represented by formula (5), a fatty acid represented by formula (6) and a glyceride represented by formula (7):

$R^{16}$—OH  (5)

$R^{17}$—COOH (6)

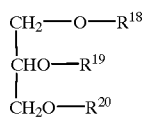
(7)

wherein
$R^{16}$ a $C_{12-22}$ alkyl or alkenyl group,
$R^{17}$ is a $C_{11-21}$ alkyl or alkenyl group and,
at least one of $R^{18}$, $R^{19}$ and $R^{20}$ is a carbonyl group having a $C_{11-21}$ alkyl or alkenyl group and the other(s) each represents a hydrogen atom.

9. A volume enhancing method, comprising:
treating hair with a composition comprising (A) a cationic surfactant and (B) an organic acid or salt thereof,
wherein the organic acid or salt thereof is selected from the group consisting of 1-naphthalenesulfonic acid, 2-naphthalenesulfonic acid, oxybenzonesulfonic acid, salicylic acid, guaiazulenesulfonic acid, a salt of 1-naphthalenesulfonic acid, a salt of 2-naphthalenesulfonic acid, a salt of oxybenzonesulfonic acid, a salt of salicylic acid, a salt of guaiazulenesulfonic acid, and mixtures thereof, and
wherein an aqueous solution of 1 mM (A) and 1 mM (B) exhibits a surface tension of 40 mN/m or less at 27±0.5° C.

10. The volume enhancing method according to claim 9, wherein the cationic surfactant (A) is a quaternary ammonium salt represented by formula (1):

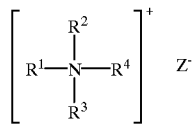
(1)

wherein
at least one of $R^1$, $R^2$, $R^3$ and $R^4$ is an alkyl or alkenyl group which may be substituted by an alkoxy, alkenyloxy, alkanoylamino or alkenoylamino group having 8 to 35 carbon atoms in total or an aliphatic acyloxy(polyethoxy)ethyl group, the other one(s) each represent a benzyl group, a $C_{1-5}$ alkyl or hydroxyalkyl group or a polyoxyethylene group;
wherein the number of repeat units of oxyethylene is not greater than 10 in total; and
$Z^-$ is a halogen ion or organic anion.

11. The volume enhancing method according to claim 9, wherein the organic acid or salt thereof is selected from the group consisting of carboxylic acid and sulfonic acid, a salt of a carboxylic acid, a salt of a sulfonic acid, and mixtures thereof.

12. The volume enhancing method according to claim 9, further comprising (C) an oil.

13. The volume enhancing method according to claim 12, wherein the oil component (C) is selected from the group consisting of an aliphatic alcohol represented by formula (5), a fatty acid represented by formula (6) and a glyceride represented by formula (7):

(5)

(6)

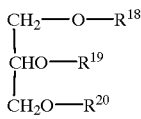(7)

wherein
$R^{16}$ is a $C_{12-22}$ alkyl or alkenyl group,
$R^{17}$ is a $C_{11-21}$ alkyl or alkenyl group and, in the formula (7),
at least one of $R^{18}$, $R^{19}$ and $R^{20}$ is a carbonyl group having a $C_{11-21}$ alkyl or alkenyl group and the other one(s) each represents a hydrogen atom.

* * * * *